United States Patent
Parsell et al.

(10) Patent No.: US 8,398,637 B2
(45) Date of Patent: Mar. 19, 2013

(54) DEVICE AND METHOD FOR LESS INVASIVE SURGICAL STABILIZATION OF PELVIC FRACTURES

(76) Inventors: Douglas Eric Parsell, Ridgeland, MS (US); Peter Alexander Cole, North Oaks, MN (US)

(*) Notice: Subject to any disclaimer, the term of this patent is extended or adjusted under 35 U.S.C. 154(b) by 775 days.

(21) Appl. No.: 11/906,849

(22) Filed: Oct. 5, 2007

(65) Prior Publication Data

US 2008/0108989 A1  May 8, 2008

Related U.S. Application Data

(60) Provisional application No. 60/856,610, filed on Nov. 6, 2006.

(51) Int. Cl.
*A61B 17/58* (2006.01)
(52) U.S. Cl. .......................... 606/71; 606/281
(58) Field of Classification Search .................. 606/103, 606/254–278, 280, 282, 53, 60, 70, 71
See application file for complete search history.

(56) References Cited

U.S. PATENT DOCUMENTS

| | | | | |
|---|---|---|---|---|
| 2,406,832 A * | 9/1946 | Hardinge | ..................... | 606/71 |
| 2,443,363 A * | 6/1948 | Townsend et al. | ............... | 606/71 |
| 2,486,303 A * | 10/1949 | Longfellow | ..................... | 606/71 |
| 3,242,922 A * | 3/1966 | Thomas | ......................... | 606/250 |
| 3,488,779 A * | 1/1970 | Christensen | ............... | 623/16.11 |
| 3,547,114 A * | 12/1970 | Haboush | ........................ | 606/71 |
| 3,900,025 A * | 8/1975 | Barnes, Jr. | ..................... | 606/71 |
| 4,292,964 A | 10/1981 | Ulrich | | |
| 4,327,715 A * | 5/1982 | Corvisier | ........................ | 606/71 |
| 4,361,144 A | 11/1982 | Slatis | | |
| 4,454,876 A * | 6/1984 | Mears | ............................ | 606/281 |
| 4,573,454 A * | 3/1986 | Hoffman | ........................ | 606/250 |
| 4,573,458 A * | 3/1986 | Lower | ............................ | 606/280 |
| 4,719,905 A * | 1/1988 | Steffee | .......................... | 606/262 |
| 5,108,397 A * | 4/1992 | White | ............................ | 606/60 |
| 5,336,224 A * | 8/1994 | Selman | ........................ | 606/280 |
| 5,350,378 A | 9/1994 | Cole | | |
| 5,443,465 A * | 8/1995 | Pennig | ........................... | 606/59 |
| 5,490,851 A * | 2/1996 | Nenov et al. | ................... | 606/252 |
| 5,507,745 A * | 4/1996 | Logroscino et al. | .......... | 606/261 |
| 5,527,310 A * | 6/1996 | Cole et al. | ....................... | 606/60 |
| 5,582,612 A * | 12/1996 | Lin | ................................ | 606/250 |
| 5,800,434 A * | 9/1998 | Campbell, Jr. | .................. | 606/279 |
| 5,810,815 A * | 9/1998 | Morales | ......................... | 606/250 |
| 5,993,449 A * | 11/1999 | Schlapfer et al. | ................ | 606/60 |
| 6,129,728 A * | 10/2000 | Schumacher et al. | .......... | 606/71 |
| 6,162,222 A | 12/2000 | Poka | | |
| 6,183,476 B1 * | 2/2001 | Gerhardt et al. | ................. | 606/71 |
| 6,336,927 B2 * | 1/2002 | Rogozinski | .................... | 606/286 |
| 6,340,362 B1 | 1/2002 | Pierer | | |
| 6,440,131 B1 | 8/2002 | Haidukewych | | |
| 6,547,790 B2 * | 4/2003 | Harkey et al. | .................. | 606/250 |
| 6,589,250 B2 * | 7/2003 | Schendel | ........................ | 606/105 |
| 6,832,999 B2 * | 12/2004 | Ueyama et al. | ................ | 606/264 |

(Continued)

OTHER PUBLICATIONS

Timothy G. Hiesterman, DO, Brian W. Hill MD, Peter A Cole MD, Surgical Technique: A percutaneous Method of Subcutaneous Fixation for the Anterior Pelvic Ring, Clinical Orthopaedics and Related Researct (2012) 470:2116-2123.*

*Primary Examiner* — Eduardo C Robert
*Assistant Examiner* — Lynnsy Schneider
(74) *Attorney, Agent, or Firm* — Workman Nydegger

(57) ABSTRACT

An apparatus and method for minimally invasive stabilization of anterior pelvic fractures consisting of two rod shaped implants that may be surgically inserted subcutaneously or along the bone surface of each hemipelvis and a means of both linking the individual rods as well as rigidly securing the construct to the pelvis.

17 Claims, 11 Drawing Sheets

U.S. PATENT DOCUMENTS

| | | | |
|---|---|---|---|
| 7,090,676 B2* | 8/2006 | Huebner et al. | 606/71 |
| 7,156,847 B2* | 1/2007 | Abramson | 606/60 |
| 7,175,622 B2* | 2/2007 | Farris | 606/250 |
| 7,322,987 B2* | 1/2008 | Schendel | 606/105 |
| 7,326,212 B2* | 2/2008 | Huebner | 606/328 |
| 7,361,177 B2* | 4/2008 | Capanni | 606/274 |
| 7,547,305 B2* | 6/2009 | Rapp | 606/70 |
| 2004/0102778 A1* | 5/2004 | Huebner et al. | 606/71 |
| 2004/0153070 A1* | 8/2004 | Barker et al. | 606/61 |
| 2005/0101959 A1* | 5/2005 | Mitkovic | 606/69 |
| 2005/0228376 A1* | 10/2005 | Boomer et al. | 606/61 |
| 2005/0228378 A1* | 10/2005 | Kalfas et al. | 606/61 |
| 2005/0277926 A1* | 12/2005 | Farris | 606/61 |
| 2005/0277932 A1* | 12/2005 | Farris | 606/61 |
| 2005/0288669 A1* | 12/2005 | Abdou | 606/61 |
| 2006/0122606 A1* | 6/2006 | Wolgen | 606/71 |
| 2006/0195087 A1* | 8/2006 | Sacher et al. | 606/61 |
| 2006/0195088 A1* | 8/2006 | Sacher et al. | 606/61 |
| 2006/0229610 A1* | 10/2006 | Piehl | 606/61 |
| 2006/0229611 A1* | 10/2006 | Avery et al. | 606/61 |
| 2006/0247627 A1* | 11/2006 | Farris | 606/61 |
| 2007/0173825 A1* | 7/2007 | Sharifi-Mehr et al. | 606/61 |
| 2007/0233070 A1* | 10/2007 | Young | 606/61 |
| 2007/0270803 A1* | 11/2007 | Giger et al. | 606/60 |
| 2007/0276405 A1* | 11/2007 | Huebner et al. | 606/105 |
| 2008/0033434 A1* | 2/2008 | Boomer et al. | 606/61 |
| 2008/0077133 A1* | 3/2008 | Schulze | 606/60 |
| 2008/0082101 A1* | 4/2008 | Reisberg | 606/60 |
| 2008/0234742 A1* | 9/2008 | Cascarino | 606/257 |
| 2008/0234743 A1* | 9/2008 | Marik | 606/257 |
| 2008/0262553 A1* | 10/2008 | Hawkins et al. | 606/278 |
| 2008/0281362 A1* | 11/2008 | Lemoine | 606/261 |
| 2009/0069851 A1* | 3/2009 | Gillard et al. | 606/280 |
| 2009/0112262 A1* | 4/2009 | Pool et al. | 606/246 |
| 2009/0177232 A1* | 7/2009 | Kiester | 606/260 |
| 2009/0204156 A1* | 8/2009 | McClintock et al. | 606/278 |
| 2009/0222042 A1* | 9/2009 | Firkins et al. | 606/246 |

* cited by examiner

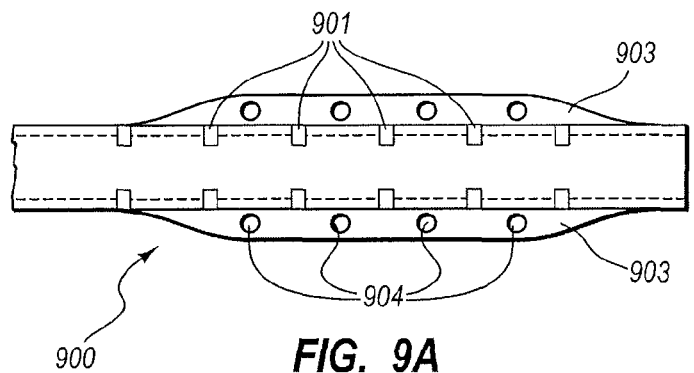
FIG. 9A
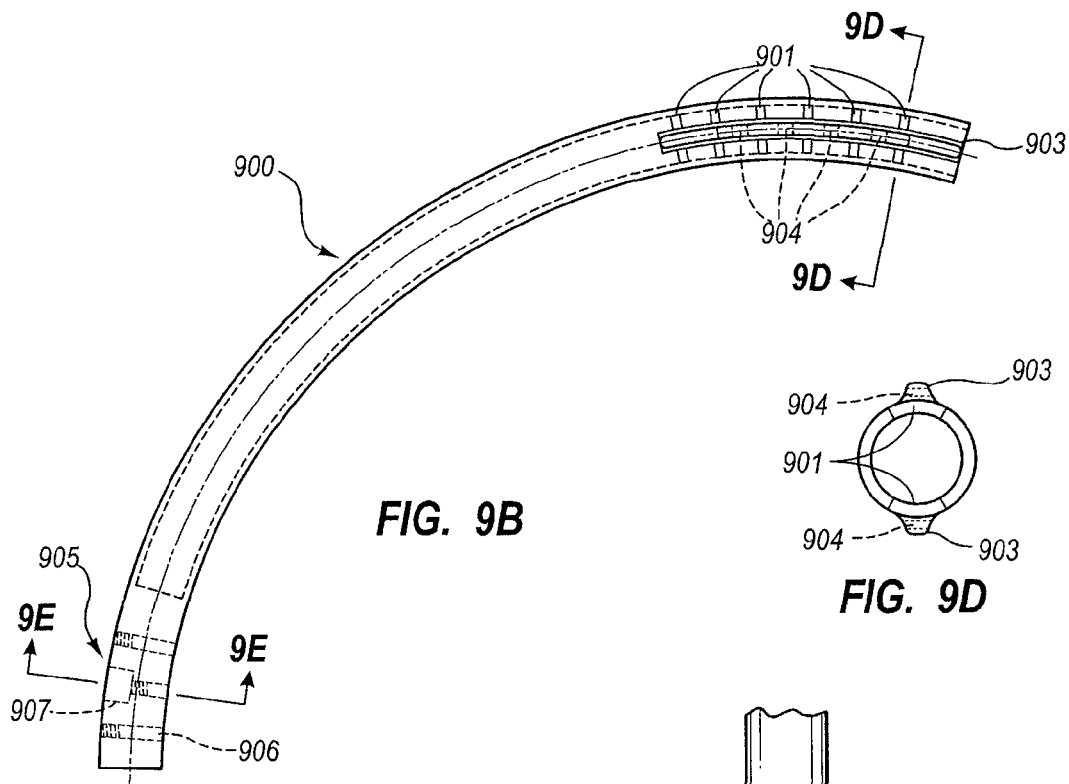
FIG. 9B
FIG. 9D
FIG. 9E
FIG. 9F

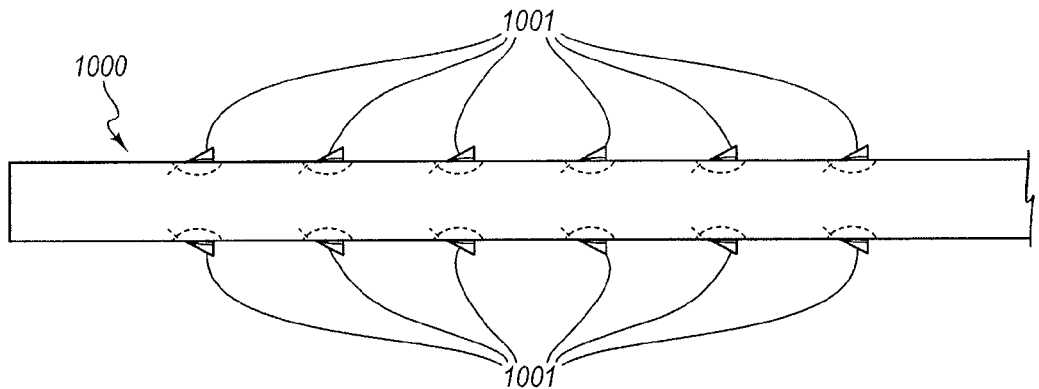
FIG. 10A
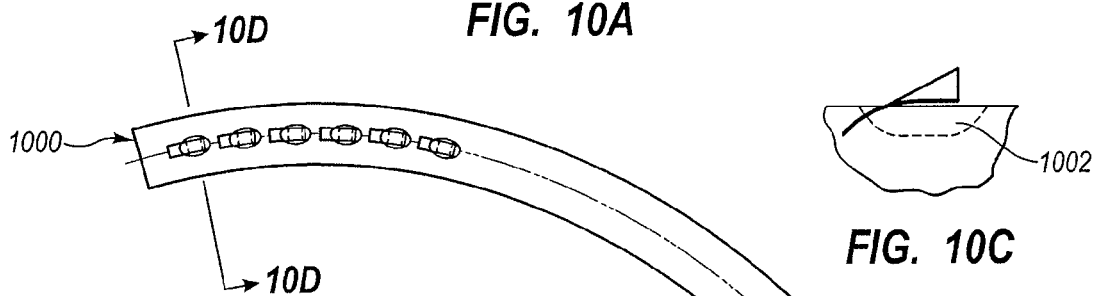
FIG. 10C
FIG. 10B
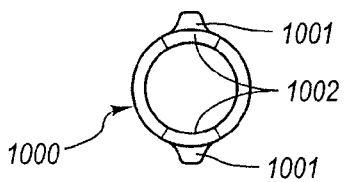
FIG. 10D
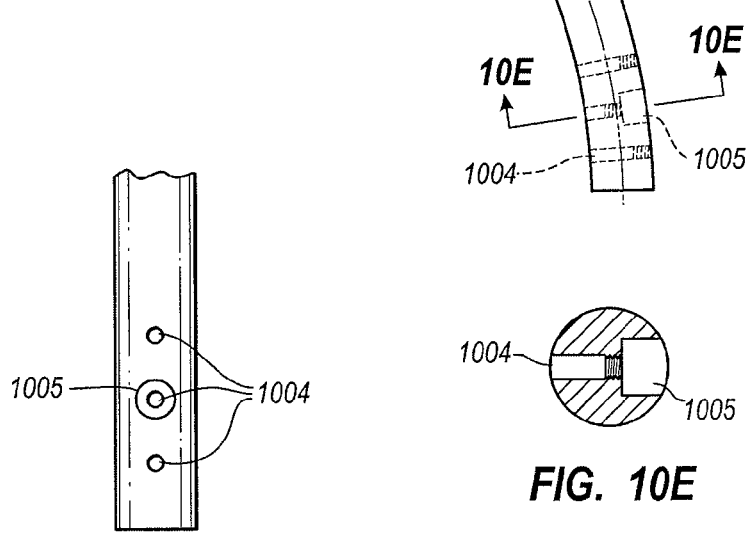
FIG. 10F
FIG. 10E

DEVICE AND METHOD FOR LESS INVASIVE SURGICAL STABILIZATION OF PELVIC FRACTURES

CROSS-REFERENCE TO RELATED APPLICATIONS

This application claims the benefit of U.S. Provisional Application No. 60/856,610 filed Nov. 6, 2006.

BACKGROUND OF THE INVENTION

1. The Field of the Invention

This invention relates to an implantable plate and/or rod system and its associated hardware used for the operation of implantation that is utilized to stabilize pelvic fractures.

2. Description of the Prior Art

Devices used to treat fracture of the pelvis currently fall under two general classifications; internal fixation and external fixation. Internal fixation is typically utilized when the patient exhibits unstable posterior pelvic fractures. See, for example, U.S. Pat. Nos. 4,454,876; 5,108,397; 6,340,362 and 6,440,131. This type of fracture tends to be more complex with it involving multiple bony structures. Internal fixation addresses these clinical issues through open reduction and correction of misaligned bone segments that are subsequently stabilized with a wide variety of plate and screw methods.

Anterior pelvic fractures or hemodynamically unstable patients are candidates for external fixation. See, for example, U.S. Pat. Nos. 4,292,964; 4,361,144; 5,350,378 and 6,162,222. External fixation consists of stabilizing the pelvic ring with a rigid framework residing outside the patient's body that is connected to the patient's pelvis via multiple pins that penetrate through the patient's soft and hard tissues. Several frame types are currently utilized. Two of the more widely deployed devices for external pelvic stabilization are the Hoffmann 2 Inverted "A" Frame and the Ganz Pelvic C Clamp.

The application of external reduction and fixation for pelvic fractures is advantageous compared to internal reduction and fixation due to its speed of deployment and lower level of technical training required for utilization. The primary disadvantages of external fixation of pelvic fractures include high risk of pin tract infections, general patient discomfort with external frame, physically blocks subsequent surgery on the abdomen and difficult to fit obese patients. The disclosed system maintains many of the advantages of external fixation while eliminating the previously associated disadvantages.

It is the goal of the disclosed invention to provide a surgical hardware system that will allow for submuscular or supramuscular/subcutaneous internal fixation of anterior pelvic instability through a minimally invasive surgical approach.

BRIEF SUMMARY OF THE INVENTION

It is herein disclosed a method for stabilization of anterior pelvic fractures consisting of an orthopedic hardware system that may be positioned between the skin and the muscle of the patient's lower torso or alternatively along the pelvic bone surface and a series of attachment devices that rigidly fix said hardware system to the bony structures of the patient's pelvis. In its preferred embodiment, the hardware system consists of two elongated members that when joined together form a framework that encompasses the anterior elements of the pelvis.

The design and curvature of the two elongated members is such so as to facilitate their insertion and advancement between the skin and the muscle of the patient's lower torso or along the bony surface of the pelvis. The elongated members may also contain contours so as to ensure clearance of critical anatomical features located within the inguinal canal such as the femoral nerve, artery and vein. The location of elongated member's insertion is either over each of the patient's anterior inferior iliac spine prominences or iliac crest. The surgeon then slides the elongated member around the anterior portion of the pelvis. The depth of the elongated member during advancement is subcutaneous and supramuscular or submuscular. Elongated member advancement is complete when the distal end of the device is positioned above the patient's pubis. Elongated members are inserted from both right and left sides.

The elongated members may be in the general shape of rods or plates. In one embodiment, the right and left elongated members are linked over the patient's pubic symphysis by way of interlocking ends and multiple screw or pin placement. An alternative embodiment links the two elongated members together at the pubis through application of a clamp device that accepts both device ends. Another alternative embodiment links the elongated member ends via a progressive interlocking produced by spring-loaded tabs along the male component engaging cut-out slots along the female component. A further embodiment links the two device halves through a cable driven screw advancement. A final embodiment links the two device halves through attachment of a cable linking the two medial ends of the anchored plates and external tensioning of the cable.

Device stabilization to the pelvis is obtained through insertion of multiple screws or pins through the lateral device ends and into the bone of the anterior inferior iliac spine or iliac crest. Additional fixation of the device to the pelvis may be obtained through insertion of multiple screws or pins through the clamp connecting means and into the underlying bone of the pubis region. Manipulation of the pelvic halves to obtain fracture reduction and plate joining may be accomplished through external loading applied via Schanz pins placed in the lateral portion of each plate half.

BRIEF DESCRIPTION OF SEVERAL VIEWS OF THE DRAWINGS

FIGS. 9A-9F. Shown is the female component of the Spring Ratcheting Less Invasive Pelvic Stabilization System.

FIGS. 10A-10F. Shown is the male component of the Spring Ratcheting Less Invasive Pelvic Stabilization System.

FIGS. 13A-13F. Shown is the female component of the Thread and Screw Driven Less Invasive Pelvic Stabilization system.

DETAILED DESCRIPTION OF THE INVENTION

Figure 1:
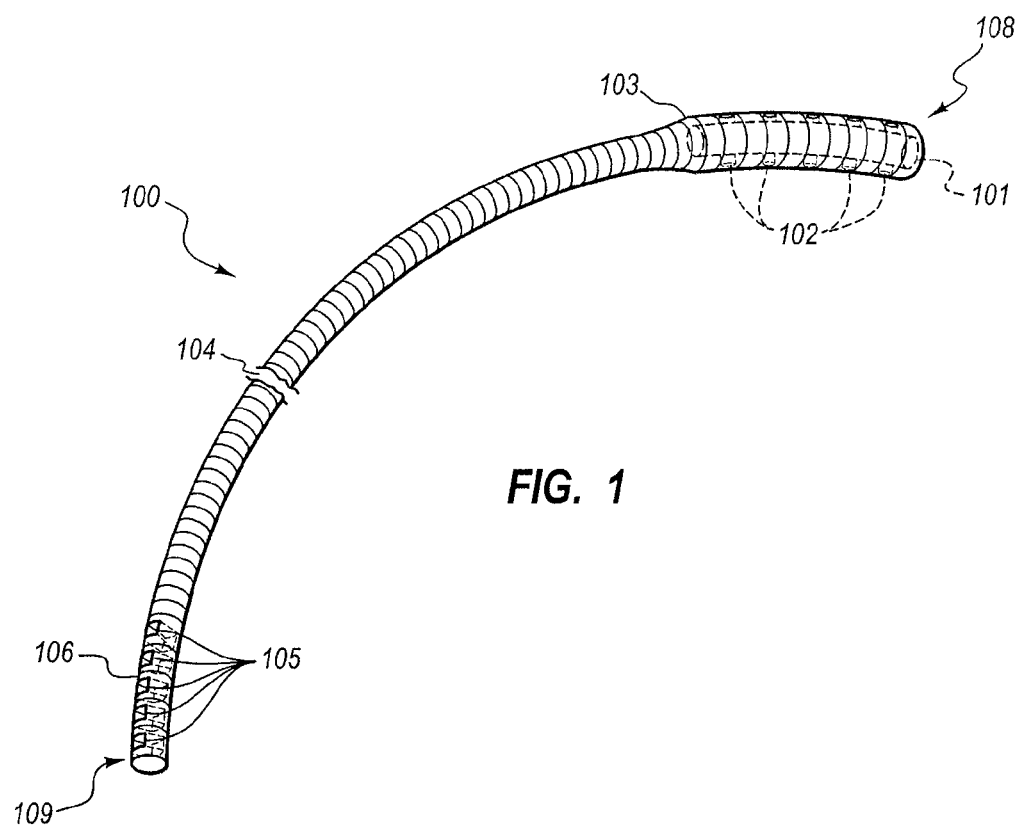
FIG. 1. Female Plate Component of the Less Invasive, Multi-Holed, Variable Positioned Locked Pelvic Stabilization System. Shown is a drawing of the female plate components of the Less Invasive Pelvic Stabilization System.

FIG. 1 illustrates the female plate components of the Less Invasive, Multi-Holed, Variable Positioned Locked Pelvic Stabilization System. The device is a smoothly arching, circular rod 100 made from typical metallic materials common to orthopedic devices such as stainless steel and titanium alloys. The medial end 108 of the device 100 expands to a radius 103 greater than that of the remaining rod section 100 to allow interconnection with the male component of the plate system. At the medial end 108 of the female plate, a circular opening 101 leading to a hollow section within the rod 100 allows the male plate to interconnect with the female plate. Multiple screw holes 102 run through the hollow, interlocking region of the female plate. The screw holes 102 may be of a standard configuration, a locking configuration or a variable angled, locking configuration. The overall length of the rod 100 will be variable 104 so as to better match the anatomical dimensions of a given patient. The distal end 109 of the rod 100 has multiple screw holes 105 to allow for mechanical connection to the bony structures of the pelvic rim. Multiple screw holes 105 are positioned at the distal rod end 109 may be of a standard configuration, a locking configuration or a variable angled, locking configuration. A circular recess 106 is positioned at the distal rod end 109 to allow for engagement of a Schanz pin connector for application of mechanical leverage during manipulation of the pelvic fracture.

Figure 2:
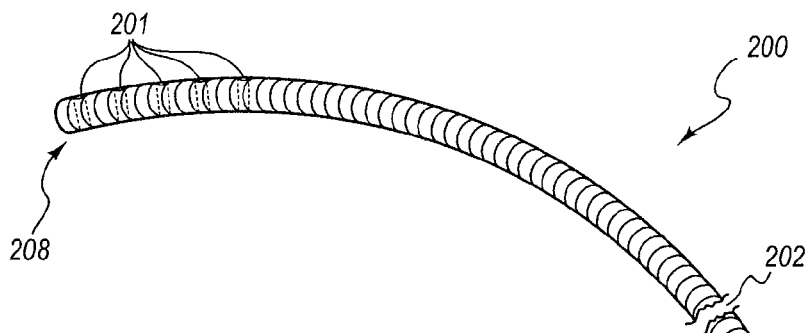
FIG. 2. Male Plate Component of the Less Invasive, Multi-Holed, Variable Positioned Locked Pelvic Stabilization System. Shown is a drawing of the male plate components of the Less Invasive Pelvic Stabilization System.

FIG. 2 illustrates the male plate components of the Less Invasive, Multi-Holed, Variable Positioned Locked Pelvic Stabilization System. The medial end 208 of the rod 200 contains multiple holes 201 to allow screws to pass through the rod 200, thus anchoring it to the female plate and to the underlying bony structures. As with the female rod 100, the rod length is variable 202 to match a wide range of patient sizes. Identical to the female rod, screw holes 203 and Schanz pin connectors 204 are located at the distal rod end 209.

Figure 3A:
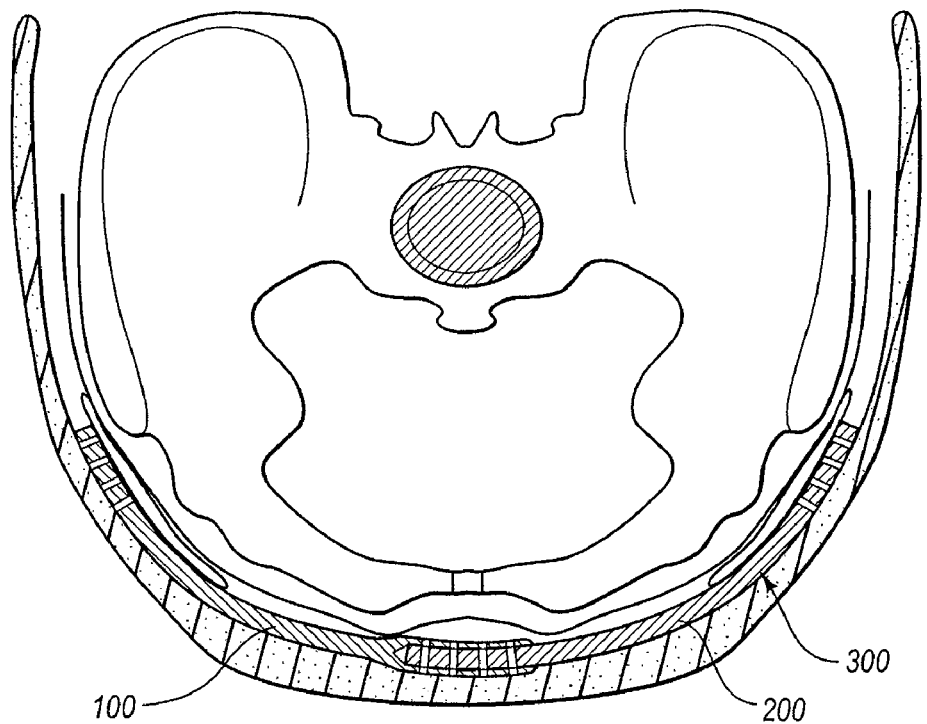
FIGS. 3A-3B. Male and Female Component of the Less Invasive, Multi-Holed, Variable Positioned Locked Pelvic Stabilization System. Shown is a drawing of the male and female components of the Less Invasive Pelvic Stabilization System joined together in a configuration as would be utilized clinically.
Figure 3B:
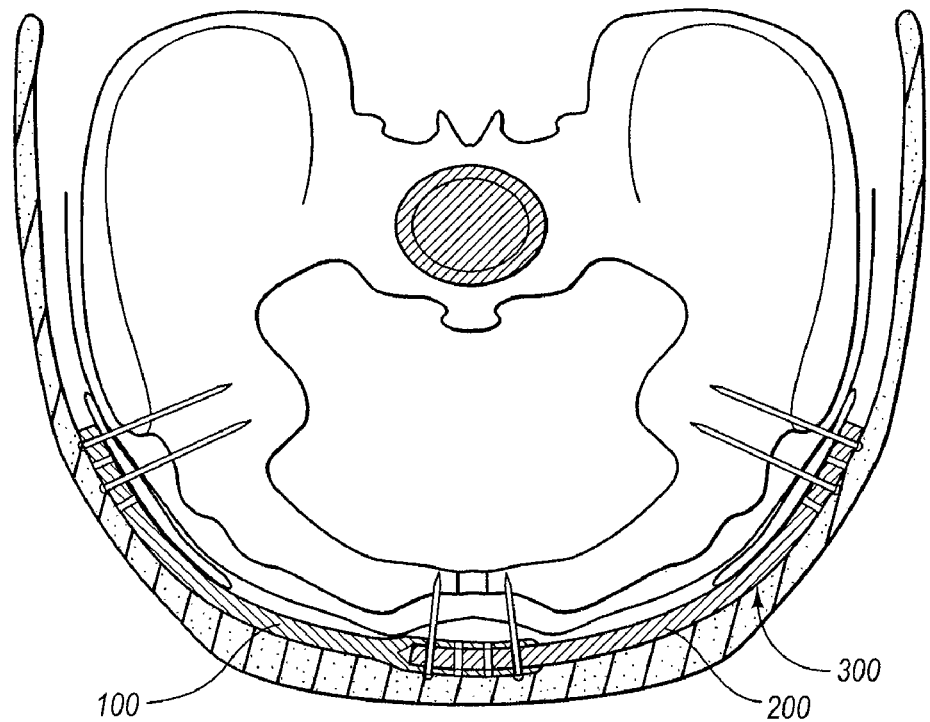

FIGS. 3A-3B illustrate the fully joined positions of the male 200 and female 100 rods, which comprise connecting means for rigidly connecting the medial ends of the male and female plate components. When the two components are linked they form a stable arch 300 that spans the ventral aspect of the patient's pelvis. Linkage of this stable construct to the fractured pelvis controls both halves of the pelvis and therefore stabilizes the fracture.

Figure 4:
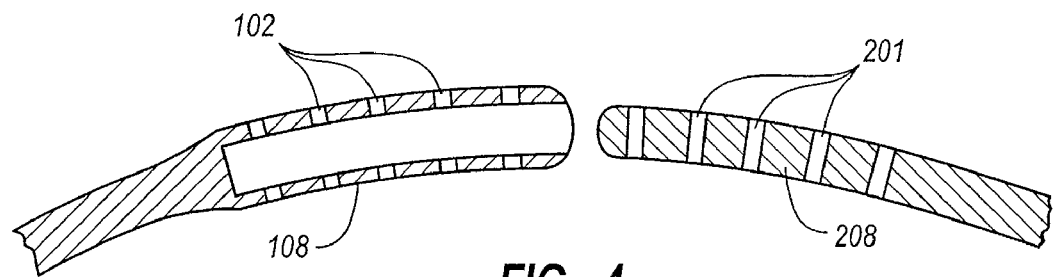
FIG. 4. Close-up of the interlocking components of the Less Invasive, Multi-Holed, Variable Positioned Locked Pelvic Stabilization System. Shown is a drawing of the male and female plate components prior to joining.

FIG. 4 illustrates a close-up view of the medial ends 108, 208 of both the female 100 and male 200 rod components as they would approach each other prior to interlocking. Both the male 200 and female 100 rods have a series of matching screw holes 105, 203 along their distal ends.

Figure 5:
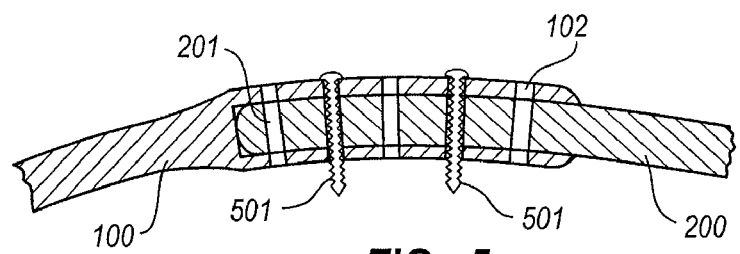
FIG. 5. Close-up of the interlocking components of the Less Invasive, Multi-Holed, Variable Positioned Locked Pelvic. Stabilization System in a fully interlocked configuration.

FIG. 5 illustrates an expanded view of the female 100 and male 200 rod components fully interlocked. Two bone screws 501 are shown traveling through aligned screw holes 201, 102 in both the male 200 and female 100 rod components. The bone screws 501 path through the linked hardware and into the underlying pelvic bone.

Figure 6:
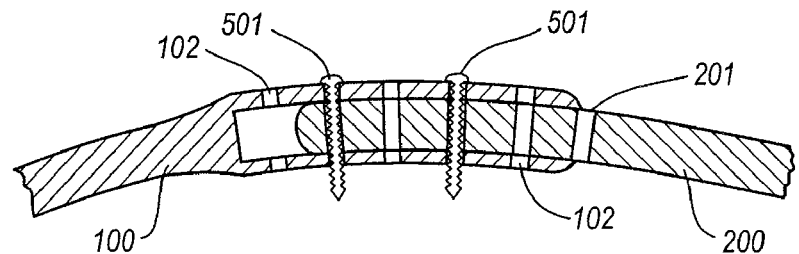
FIG. 6. Close-up of the interlocking components of the Less Invasive, Multi-Holed, Variable Positioned Locked Pelvic Stabilization System in a slightly less than fully interlocked configuration.

FIG. 6 illustrates an expanded view of the female 100 and male 200 rod components slightly retracted from a fully interlocked position. Bone screws 501 are inserted through the pair of interconnected rods 100, 200 in the same positions as the fully interconnected rod configuration. Alternative screw positions are available as warranted by the position of dense bone for reception for the protruding bone screw 501.

Figure 7:
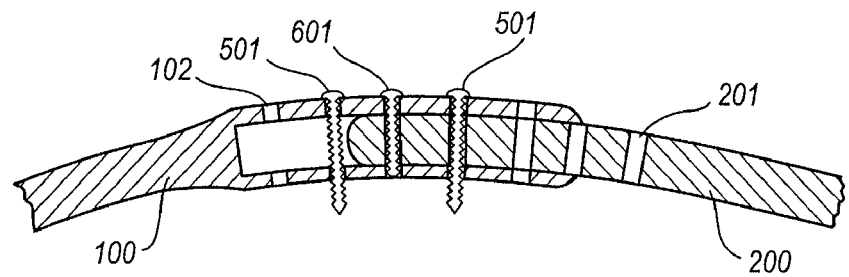
FIG. 7. Close-up of the interlocking components of the Less Invasive, Multi-Holed, Variable Positioned Locked Pelvic Stabilization System in an interlocked configuration that is one-half of fully interlocked.

FIG. 7 illustrates an expanded view of the female 100 and male 200 rod components in a position that is approximately one-half interlocked. Two full length screws 501 are utilized to attach the pelvic LISS hardware to the underlying pelvic bone while a third non-penetrating, inter-rod screw 601 is placed centrally to aid in the mechanical interlocking of the male 200 and female 100 rods.

Figure 8:
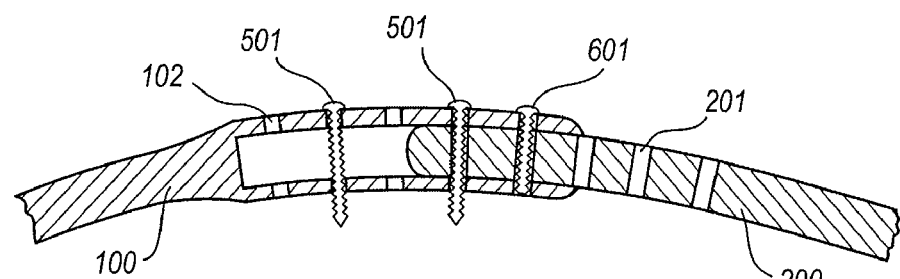
FIG. 8. Close-up of the interlocking components of the Less Invasive, Multi-Holed, Variable Positioned Locked Pelvic Stabilization System in a minimally interlocked configuration.

FIG. 8 illustrates an expanded view of the female 100 and male 200 rod components in a configuration of minimal interlocking. The female 100 and male 200 rod components are mechanically joined via two bone screws 501 and one inter-rod screw 601.

FIGS. 9A-9F illustrate the female component 900 of the Spring Ratcheting Less Invasive Pelvic Stabilization System. Unique features of the female component 900 of the Spring Ratcheting Less Invasive Pelvic Stabilization System include a series of slots 901 through the sidewall of the rod 900 that are positioned at the male entry end 902 of the component. The function of these slots 901 is to allow mechanical retention of tabbed leaf springs 1001 embedded along the received male component 1000 (see FIGS. 10A-10B). Also present at the receiving end 902 of the rod 900 are two dorsal and pectoral flanges 903 containing locking screw holes 904. Locking screws are inserted through these holes 904 to help mechanically secure the pelvic LISS to the patient's pubic symphysis bone. As with the alternative embodiments of the pelvic LISS, the distal, non-receiving end 905 of the female component 900 consists of multiple locking screw holes 906 and a Schanz pin engagement port 907.

FIGS. 10A-10F illustrate the male component 1000 of the Spring Ratcheting Less Invasive Pelvic Stabilization System. Unique features of the male component 1000 of the Spring Ratcheting Less Invasive Pelvic Stabilization System include a series of tabbed leaf springs 1001 embedded along the surface of the lateral portion of the component. Upon insertion into the female component 900, the tabbed leaf springs 1001 are compressed. With further insertion, the tabbed leaf springs 1001 engage with the slots 901 along the female component 900. Successive insertion is possible to facilitate further fracture reduction while disengagement will be mechanically impeded due to the interlocking of the leaf spring/slot combination. The slots 901 and tabbed leaf springs 1001 comprise connecting means for rigidly connecting the male and female components together. As with the alternative embodiments of the pelvic LISS, the distal end of the male component consists of multiple locking screw holes 1004 and a Schanz pin engagement port 1005.

Figure 11A:
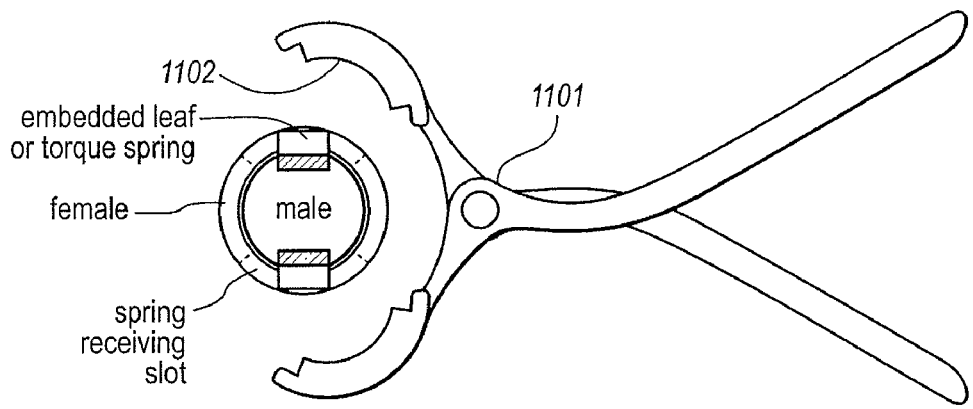
FIGS. 11A-11C. Shown is the release clamp used to disengage the male and female plate components of the Spring Ratcheting Less Invasive Pelvic Stabilization System.
Figure 11B:
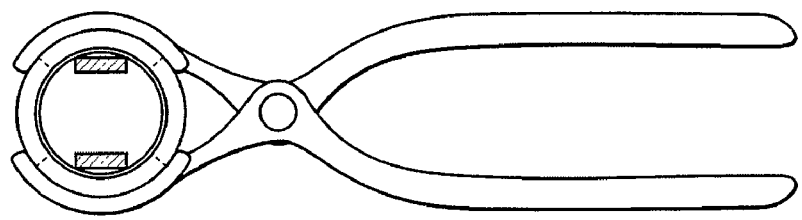
Figure 11C:
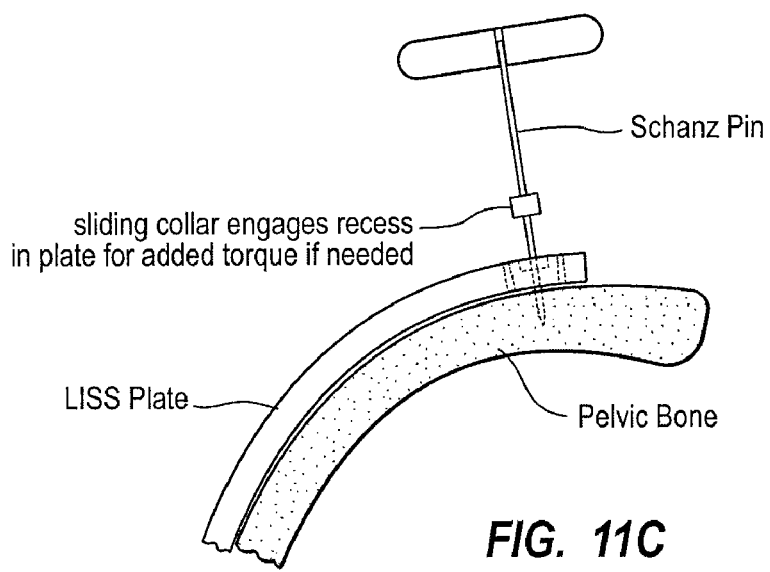
Figure 12A:
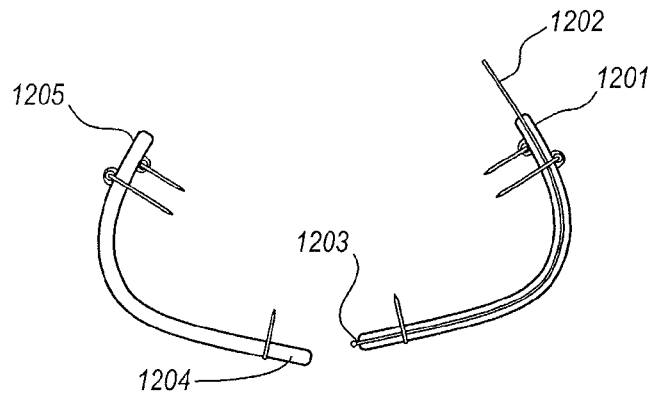
FIGS. 12A-12D. Shown is the Cable Driven Invasive Pelvic Stabilization System.
Figure 12B:
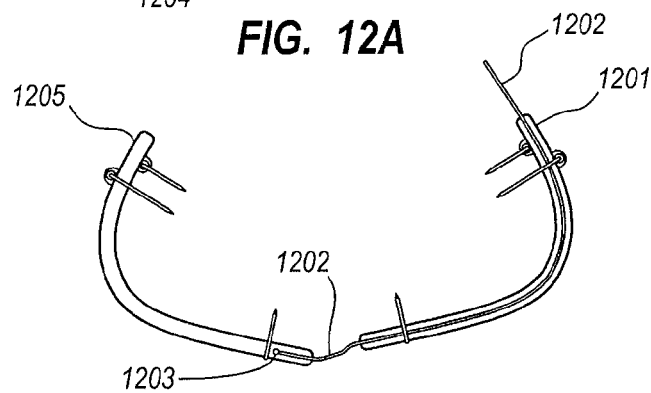
Figure 12C:
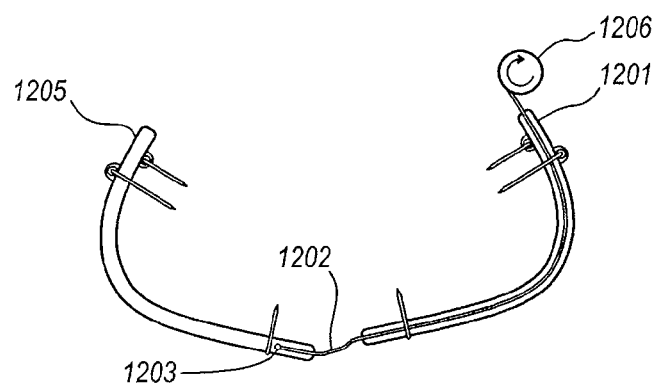
Figure 12D:
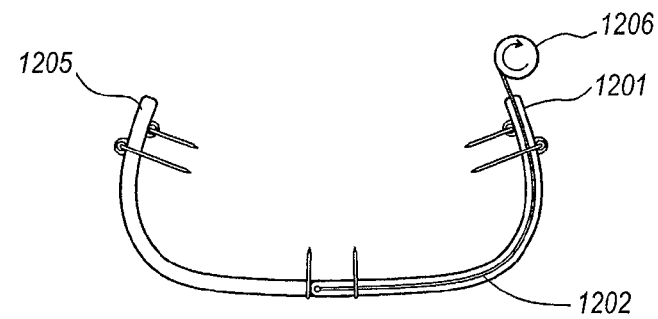

FIGS. 11A-11C illustrate the novel tools for disengaging the male and female components of the Ratcheting Less Invasive Pelvic Stabilization System. Disengagement would be clinically needed during hardware removal after bone healing has generated sufficient mechanical stability. The custom clamp device 1001 would be surgically inserted to encase the medial/linked ends of the male 1000 and female 900 plates. The insets provided along the clamp surface 1102 are designed to be of a depth sufficient to release the leaf springs 1001 of the male plate 1000 from the slots 901 of the female plate 900. Once the leaf springs 1001 are freed, the male and female plates 1000, 900 are free to disengage and for hardware removal to proceed.

FIGS. 12A-12D illustrates the Cable Driven Less Invasive Pelvic Stabilization System. The Pelvic Cable LISS could be utilized clinically as follows.

1. LISS plates are inserted subcutaneous or submuscular. Plates are anchored via screws at the iliac crest and also possibly at the pubic symphysis. One of the two plates 1201 has a hollow tunnel with a cable 1202 running along its length. The cable 1202 has an attachment feature at its end 1203 to securely capture the end 1204 of the opposing plate 1205. The attachment feature may be a locking feature such as coarse threading or a rotational interlock.
2. Once plates are secured to each hemi-pelvis in proper anatomic relation, the surgeon manipulates the cable from the end of one plate and secures it to the end of the other plate. Standard surgical instruments would be used to facilitate this maneuver.
3. Once the plates 1201, 1205 are linked through the cable 1202, the cable 1202 is tensioned at its exit point at the lateral plate end.
4. The force provided by the cable tension should close any misalignment between the pelvic halves.
5. Once the fractured pelvis is brought back into anatomic alignment, plates can be linked or additional screws placed. Whether the tensioned cable is removed once the anatomy is believed stable or the cable is left inside the construct under some degree of tension is optional.

FIGS. 13A-13F illustrate the female component 1300 of the Thread and Screw Driven Pelvic LISS. The female rod component 1300 exhibits locking screw holes 1301 well as Shanz pins connectors 1302 along its proximal end. The medial end of the female rod component exhibits a threaded inner surface 1303 for joining with the screw component of the male device and lateral flanges 1304 with a series of locking screw holes 1305.

Figure 13A:
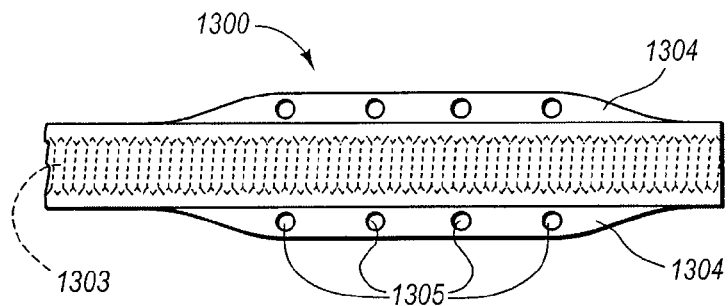
Figure 13B:
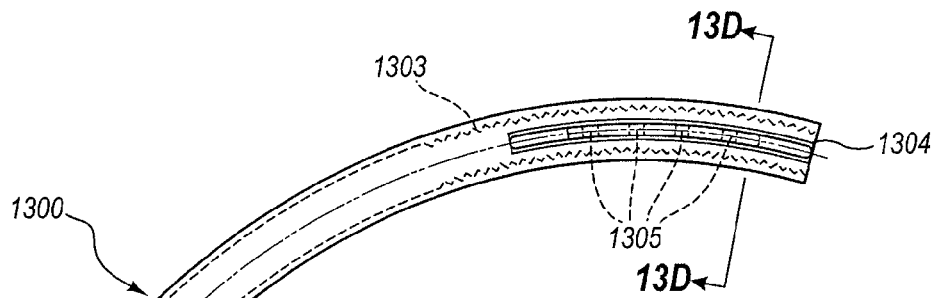
Figure 13D:
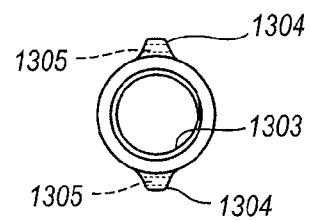
Figure 13E:
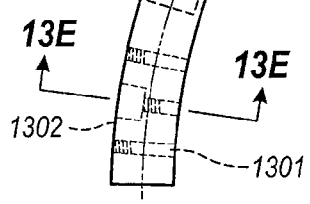
Figure 13E:
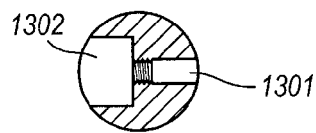
Figure 13F:
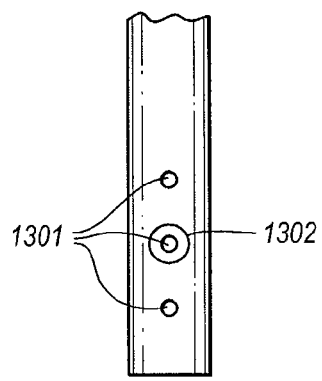
Figure 14A:
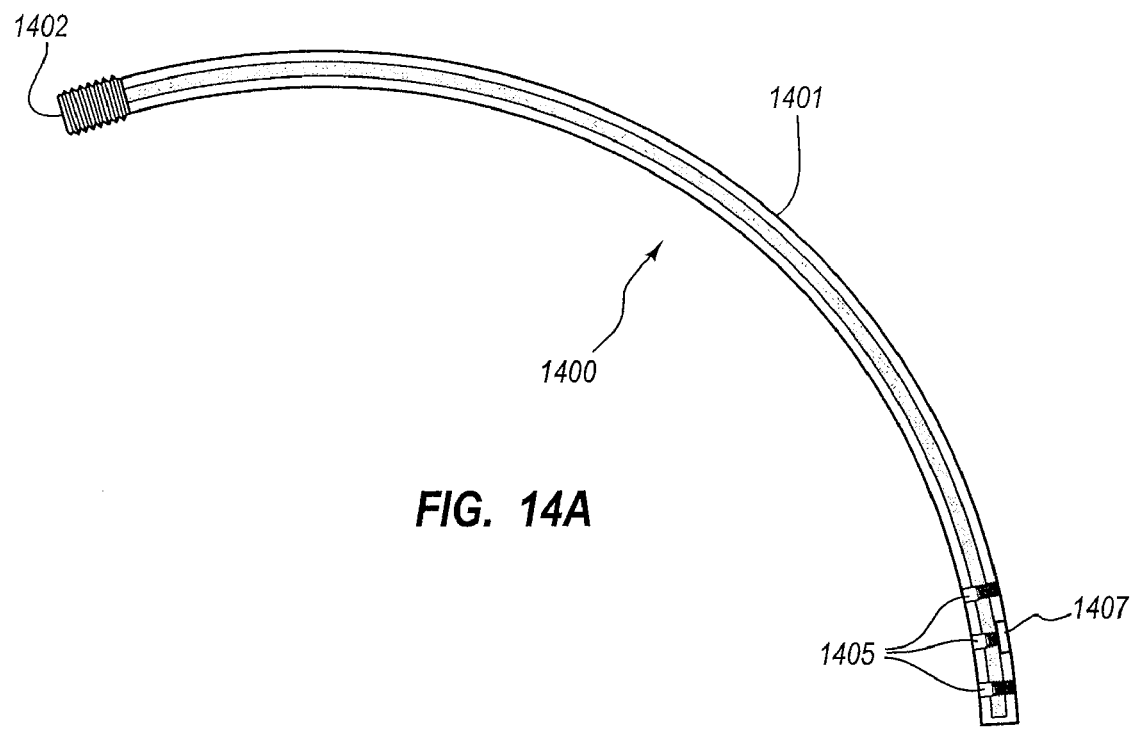
FIGS. 14A-14B. Shown is the male component of the Thread and Screw Driven Less Invasive Pelvic Stabilization system.
Figure 14B:
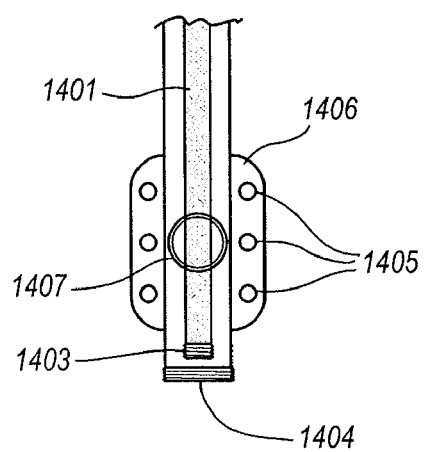

FIGS. 14A-14B illustrate the male component 1400 of the Thread and Screw Driven Pelvic LISS. The male rod component 1400 contains a flexible cable 1401 that runs along the interior length of the rod 1400. The medial end of the cable is attached to a rotating screw 1402 that is size and shape matched to engage with the female threaded medial portion 1303 of the associated female rod component 1300 (FIGS. 13A-13B). The proximal end 1403 of the cable 1401 is fitted with a mechanical means for coupling with an external, rotating drive mechanism (not shown) such as threading or a mechanical interlocking configuration. The proximal end of the male rod 1400 may be capped with a threaded end cap 1404 to limit access to bodily fluids once proper clinical fixation is obtained. Proximal attachment of the device to the patient's pelvic bone may be accomplished via insertion of bone screw through locking screw holes 1405 positioned along a lateral flange 1406. Interoperative torque may be applied to the construct as an aid in obtaining proper alignment through a Shanz pin port 1407 located toward the proximal end of the male rod component 1400. The flexible cable 1401 comprises connecting means for rigidly connecting the male and female components together.

Figure 15:
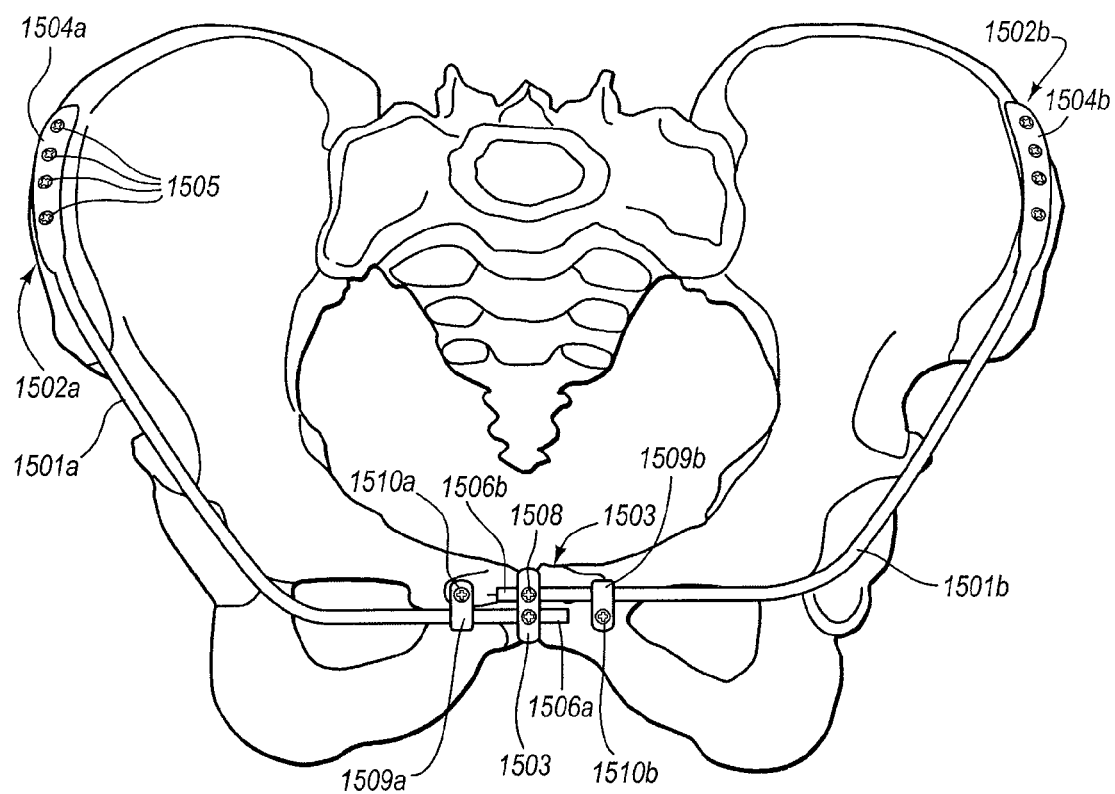
FIG. 15. Shown is a clinically usable positioning of a Clamp Adjusted Less Invasive Pelvic Stabilization system on a human pelvis.

FIG. 15 illustrates a Clamp Adjusted Pelvic Stabilization System as it would be positioned on the pelvis. On both the right and left sides of the pelvis, rods 1501 arc around the pelvis from the iliac crest 1502 to the pubic symphysis 1503. Proximal rod ends 1504 are secured to the pelvic bone via bone screws inserted through multiple, threaded screw holes 1505. Medial rod ends 1506 are secured to each other via a mechanical linkage that comprises a screw-driven, clamping device 1507, 1508 that simultaneously holds rigid left and right rods at the medial position of their overlapping. The screw-driven, clamping device 1507, 1508 comprises connecting means for rigidly connecting the medial rod ends 1506 together. Rigid fixation of the rod ends 1506 to the underlying pelvic bone is accomplished via individual right and left clamps 1509 and screws 1510 that confine said rods and rigidly hold them to the underlying pelvic bone via bone screw placement.

Figure 16A:
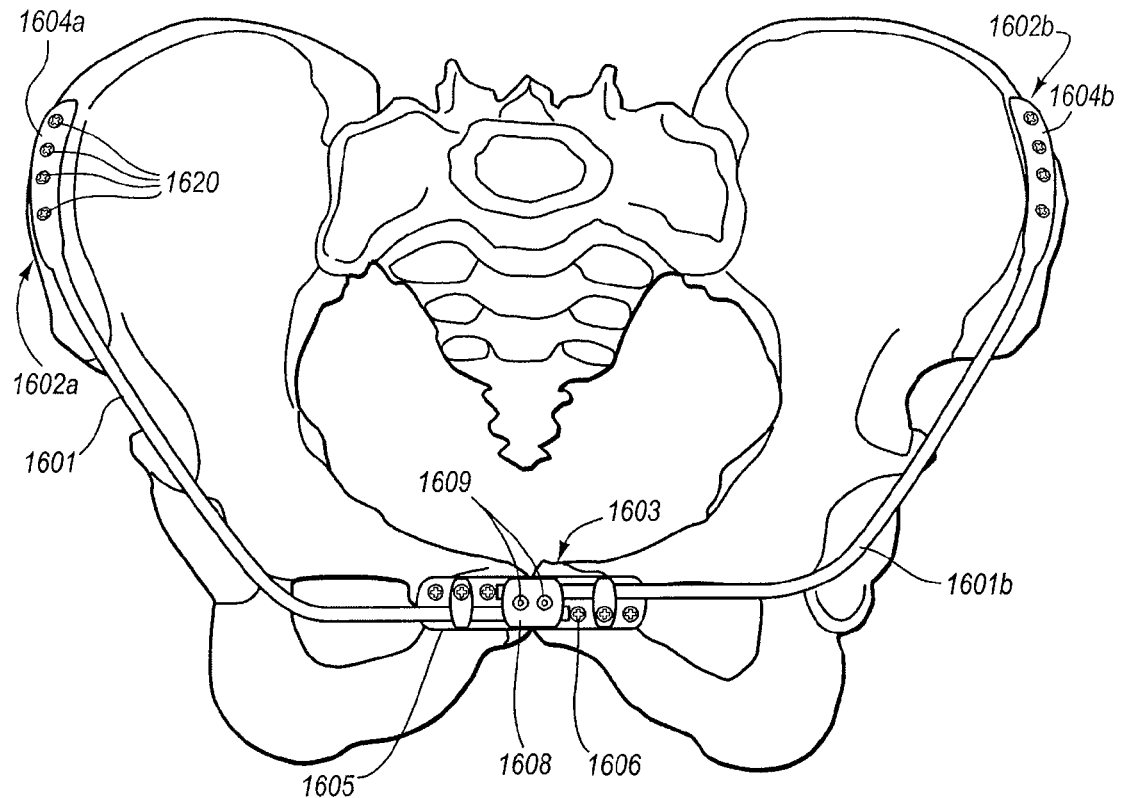
FIG. 16A. Shown is a clinically usable positioning of a Clamp/Plate Less Invasive Pelvic Stabilization system on a human pelvis.

FIG. 16A illustrates a Clamp/Plate Pelvic Stabilization System as it could be positioned on the pelvis. On both the right and left sides of the pelvis, rods 1601 arc around the pelvis from the iliac crest 1602 to the pubic symphysis 1603. Proximal rod ends are secured to the pelvic bone via bone screws inserted through multiple, threaded screw holes 1620. Across the pubic symphysis 1603, a rigid baseplate 1605 is positioned and secured through placement of multiple bone screws 1606. Dual channels along the outer surface of the plate 1605 accept the medial ends of the right and left rods 1601. A clamping plate 1608 compresses the rods 1601 into the baseplate 1605 via insertion of multiple locking screws 1609. The rigid baseplate 1605 and clamping plate 1608 together comprise connecting means for rigidly connecting the medial ends of the right and left rods 1601 together.

Figure 16B:
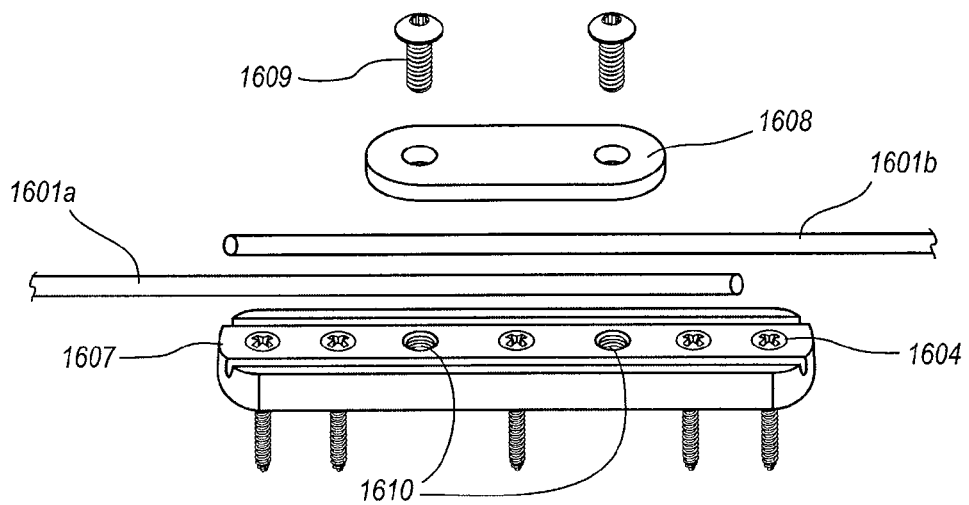
FIG. 16B. Shown is an expanded view of the medial segment for an alternative configuration of the Clamp/Plate Less Invasive Pelvic Stabilization system.
Figure 15:
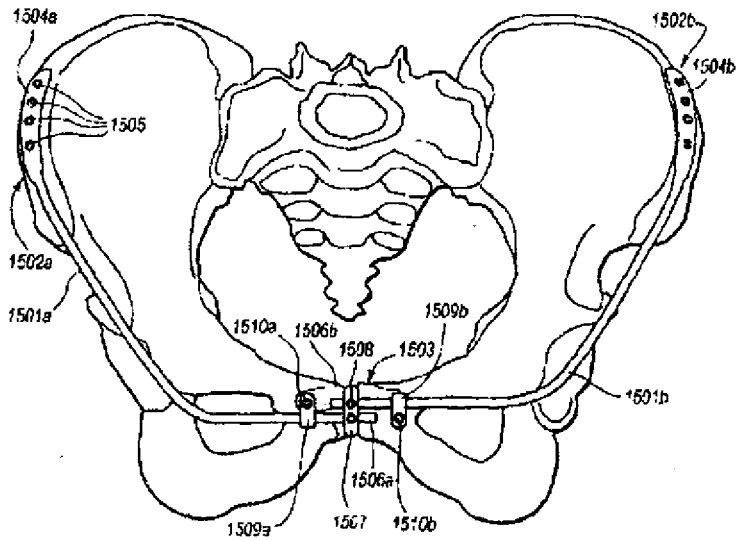

FIG. 16B illustrates an expanded view of the medial segment of an alternative format for the Clamp/Plate Pelvic Stabilization System. A plate 1607 is surgically positioned over the pelvic pubis and rigidly anchored through insertion of multiple locking bone screws 1604. The medial ends of the right and left hemipelvic rods 1601 are rigidly bound together via compressive forces applied through placement of a capping plate 1608 and insertion and tightening of screws 1609 that travel through the capping plate 1608 and engage with threaded screw holes 1610 within the larger plate 1607 positioned beneath. The plate 1607 and capping plate 1608 together comprise connecting means for rigidly connecting the medial ends of the right and left hemipelvic rods 1601 together.

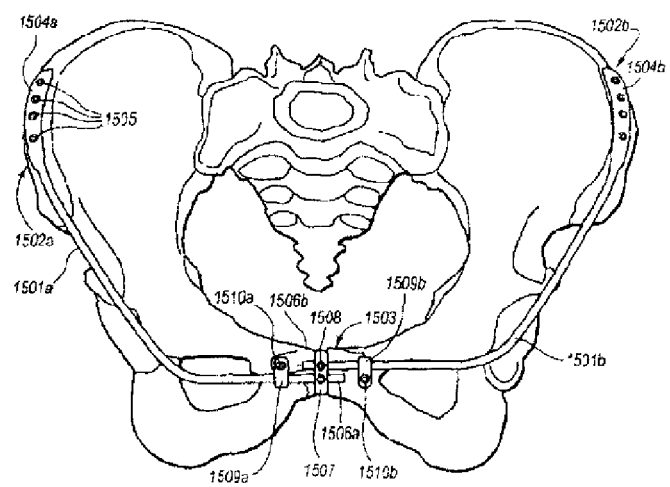

We claim the following:

1. A pelvic fracture stabilization device for orthopedic stabilization of a fracture or fractures in a human pelvis and that is implantable beneath a patient's skin and above the patient's muscle or below the patient's muscle against a surface of the patient's bone, the device comprising:

a first implant member adapted so as to facilitate subcutaneous and supramuscular or submuscular insertion and advancement of the first implant member and positioning adjacent to a right hemipelvis of a human pelvic bone, the first implant member further having a length so as to span from a location along a right iliac bone to a pubic symphysis of a human pelvic bone and a curvature so as to generally follow a curvature of an adjacent right iliac bone; and a second implant member initially separate and detached from the first implant member and adapted so as to facilitate subcutaneous and supramuscular or submuscular insertion and advancement of the second implant member and positioning adjacent to a left hemipelvis of a human pelvic bone independent of insertion and advancement of the first implant member, the second implant member further having a length so as to span from a location along a left iliac bone to a pubic symphysis of a human pelvic bone and a curvature so as to generally follow a curvature of an adjacent left iliac bone;

one or more holes in a first proximal end of the first implant member for use in rigidly attaching the first proximal end of the first implant member at a location along a right iliac bone of a right hemipelvis;

one or more holes in a second proximal end of the second implant member for use in rigidly attaching the second proximal end of the second implant member at a location along a left iliac bone of a left hemipelvis; and a clamp for rigidly connecting a first medial end of the first implant member with a second medial end of the second implant member at a pubic symphysis after independent insertion and advancement of the first and second implant members so that the first and second implant members maintain a curvature and relative structural positioning so as to stabilize a human pelvis when in use and so that a first end of the clamp is secured to the first medial end of the first implant member and a second end of the clamp is secured to the second medial end of the second implant member in order that the first and second medial ends are spaced apart, substantially parallel, and extend in opposing directions.

2. The pelvic fracture stabilization device according to claim 1, further comprising screws for securing the clamp to the first and second medial ends.

3. The pelvic fracture stabilization device according to claim 1, further comprising screws for securing the clamp to bone in the pubic symphysis region of a human pelvic bone.

4. The pelvic fracture stabilization device according to claim 1, further comprising a first bracket for securing the first medial end of the first implant member to bone in the pubic symphysis region of the right hemipelvis and a second bracket for securing the second medial end of the second implant member to bone in the pubic symphysis region of the right hemipelvis.

5. The pelvic fracture stabilization device according to claim 1, wherein the clamp comprises a base plate and a clamping plate.

6. The pelvic fracture stabilization device according to claim 1, the clamp comprising a rigid plate surgically positionable between and attachable to the first and second medial ends and also to bone in the pubic symphysis region of the pelvic bone.

7. The pelvic fracture stabilization device according to claim 1, wherein the elongated implant members are rod-shaped, have a substantially circular cross section, and are substantially devoid of lateral protuberances.

8. The pelvic fracture stabilization device according to claim 1, wherein the elongated implant members are plate-shaped and substantially devoid of lateral protuberances.

9. The pelvic fracture stabilization device according to claim 1, wherein the first implant member has a length so as to span from a right anterior inferior iliac spine of a right iliac bone to a pubic symphysis of a human pelvic bone and a curvature so as to generally follow a curvature of an adjacent right iliac bone, and wherein the second implant member has a length so as to span from a left iliac bone to a pubic symphysis of a human pelvic bone and a curvature so as to generally follow a curvature of an adjacent left anterior inferior iliac spine of a left iliac bone.

10. The pelvic fracture stabilization device according to claim 1, wherein the first implant member has a length so as to span from a right iliac crest of a right iliac bone to a pubic symphysis of a human pelvic bone and a curvature so as to generally follow a curvature of an adjacent right iliac bone, and wherein the second implant member has a length so as to span from a left iliac crest of a left iliac bone to a pubic symphysis of a human pelvic bone and a curvature so as to generally follow a curvature of an adjacent left iliac bone.

11. A pelvic fracture stabilization device for orthopedic stabilization of a fracture in a human pelvis and that is implantable beneath a patient's skin and above the patient's muscle or below the patient's muscle against a surface of the patient's bone, the device comprising:

a first rod- or plate-shaped implant member that is substantially devoid of lateral protuberances so as to facilitate subcutaneous and supramuscular or submuscular insertion and advancement of the first implant member and be positionable adjacent to a right hemipelvis of a human pelvic bone, the first implant member further having a length so as to span from a location along a right iliac bone to a pubic symphysis of a human pelvic bone and a curvature so as to generally follow a curvature of an adjacent right iliac bone; and a second rod- or plate-shaped implant member initially separate and detached from the first implant member and that is substantially devoid of lateral protuberances so as to facilitate subcutaneous and supramuscular or submuscular insertion and advancement of the second implant member and be positionable adjacent a left hemipelvis of a human pelvic bone independent of insertion and advancement of the first implant member, the second implant member further having a length so as to span from a location along a left iliac bone to a pubic symphysis of a human pelvic bone and a curvature so as to generally follow a curvature of an adjacent left iliac bone;

one or more holes in a first proximal portion of the first implant member for use in rigidly attaching the first proximal portion of the first implant member at a location along a right iliac bone of a right hemipelvis;

one or more holes in a second proximal portion of the second implant member for use in rigidly attaching the proximal portion of the second implant at a location along a left iliac bone of a left hemipelvis; and at least one of a clamp or plate for rigidly connecting a first medial end of the first implant member with a second medial end of the second implant member at a pubic symphysis after independent insertion and advancement of the first and second implant members so that the first and second implant members maintain a curvature and relative structural positioning so as to stabilize a human pelvis when in use and so that a first end of the clamp or plate is secured to the first medial end of the first implant member and a second end of the clamp or plate is secured to the second medial end of the second implant member in order that the first and second medial ends are spaced apart, substantially parallel, and extend in opposing directions.

12. The pelvic fracture stabilization device according to claim 11, wherein the first implant member has a length so as to span from a right anterior inferior iliac spine of a right iliac bone to a pubic symphysis of a human pelvic bone and a curvature so as to generally follow a curvature of an adjacent right iliac bone, and wherein the second implant member has a length so as to span from a left anterior inferior iliac spine of a left iliac bone to a pubic symphysis of a human pelvic bone and a curvature so as to generally follow a curvature of an adjacent left iliac bone.

13. The pelvic fracture stabilization device according to claim 11, wherein the first implant member has a length so as to span from a right iliac crest of a right iliac bone to a pubic symphysis of a human pelvic bone and a curvature so as to generally follow a curvature of an adjacent right iliac bone, and wherein the second implant member has a length so as to span from a left iliac crest of a left iliac bone to a pubic symphysis of a human pelvic bone and a curvature so as to generally follow a curvature of an adjacent left iliac bone.

14. A pelvic fracture stabilization device for orthopedic stabilization of a fracture or fractures in a human pelvis and that is implantable beneath a patient's skin and above the patient's muscle or below the patient's muscle against a surface of the patient's bone, the device comprising:
a first implant member adapted so as to facilitate subcutaneous and supramuscular or submuscular insertion and advancement of the first implant member and positioning adjacent to a right hemipelvis of a human pelvic bone, the first implant member further having a length so as to span from a right anterior inferior iliac spine to a pubic symphysis of a human pelvic bone and a curvature so as to generally follow a curvature of an adjacent right iliac bone; and
a second implant member initially separate and detached from the first implant member and adapted so as to facilitate subcutaneous and supramuscular or submuscular insertion and advancement of the second implant member and positioning adjacent to a left hemipelvis of a human pelvic bone independent of insertion and advancement of the first implant member, the second implant member further having a length so as to span from a left anterior inferior iliac spine to a pubic symphysis of a human pelvic bone and a curvature so as to generally follow a curvature of an adjacent left iliac bone;
one or more holes in a first proximal end of the first implant member for use in rigidly attaching the first proximal end of the first implant member to a right anterior inferior iliac spine of a right hemipelvis;
one or more holes in a second proximal end of the second implant member for use in rigidly attaching the second proximal end of the second implant member to a left anterior inferior iliac spine of a left hemipelvis;
a clamp or plate for rigidly connecting a first medial end of the first implant member with a second medial end of the second implant member at a pubic symphysis after independent insertion and advancement of the first and second implant members so that the first and second implant members maintain a curvature and relative structural positioning so as to stabilize a human pelvis when in use and so that a first end of the clamp or plate is secured to the first medial end of the first implant member and a second end of the clamp or plate is secured to the second medial end of the second implant member in order that the first and second medial ends are spaced apart, substantially parallel, and extend in opposing directions;
first means for securing the first implant member to the clamp or plate; and
second means, separate from the first means, for securing the second implant member to the clamp or plate.

15. A pelvic fracture stabilization device for orthopedic stabilization of a fracture or fractures in a human pelvis and that is implantable beneath a patient's skin and above the patient's muscle or below the patient's muscle against a surface of the patient's bone, the device comprising:
a pair of initially separate and detached elongated implant members, each having a length and curvature so as to span from an iliac of a human pelvic bone to a pubic symphysis of the human pelvic bone, a first implant member being adapted so as to be positionable adjacent to a right hemipelvis of a human pelvic bone, and a second implant member being adapted so as to be positionable adjacent to a left hemipelvis of a human pelvic bone independent of and while separate and detached from the first implant;
one or more holes penetrating through a first proximal end of the first implant member for use in rigidly attaching the first proximal end of the first implant member to a bone at the iliac crest of a right hemipelvis;
one or more holes penetrating through a second proximal end of the second implant member for use in rigidly attaching the second proximal end of the second implant member to a bone at the iliac crest of a left hemipelvis; and
a clamp for rigidly connecting a first medial end of the first implant member with a second medial end of the second implant member at a pubic symphysis after independent positioning of the first and second implant members adjacent to the right hemipelvis and left hemipelvis, respectively, so that the first and second implant members maintain a curvature and relative structural positioning so as to stabilize a human pelvis when in use and so that a first end of the clamp is secured to the first medial end of the first implant member and a second end of the clamp is secured to the second medial end of the second implant member in order that the first and second medial ends are spaced apart, substantially parallel, and extend in opposing directions.

16. A method for stabilizing a pelvic fracture in a human pelvic bone, the method comprising:
inserting and advancing a first implant member subcutaneously and supramuscularly or submuscularly and positioning the first implant member adjacent to a right hemipelvis of the human pelvic bone in order for the first implant member to span from a location along a right iliac bone to a pubic symphysis of the human pelvic bone and generally follow a curvature of an adjacent right iliac bone; and
while remaining separate and detached from the first implant member, inserting and advancing a second implant member subcutaneously and supramuscularly or submuscularly and positioning the second implant adjacent to a left hemipelvis of the human pelvic bone in order for the second implant member to span from a location along a left iliac bone to the pubic symphysis of the human pelvic bone and generally follow a curvature of an adjacent left iliac bone;

rigidly attaching a first proximal portion of the first implant member at a location along the right iliac bone of the right hemipelvis by inserting screws through one or more holes in a first proximal portion of the first implant member and engaging underlying bone tissue;

rigidly attaching a second proximal portion of the second implant member at a location along the left iliac bone of the left hemipelvis by inserting screws through one or more holes in a second proximal portion of the second implant member and engaging underlying bone tissue; and after inserting and advancing of the first and second implant members while separate and detached from each other, rigidly connecting a first medial end of the first implant member with a second medial end of the second implant member at the pubic symphysis by means of at least one of a clamp or plate so that the first and second implant members maintain a curvature and relative structural positioning so as to stabilize the human pelvic bone and so that a first end of the clamp or plate is secured to the first medial end of the first implant member and a second end of the clamp or plate is secured to the second medial end of the second implant member in order that the first and second medial ends are spaced apart, substantially parallel, and extend in opposing directions.

17. A method for stabilizing a pelvic fracture in a human pelvic bone, the method comprising:

independently placing a pair of initially separate and detached elongated implant members in respective hemispheres of a human pelvic bone, a first implant member being positioned adjacent to a right hemipelvis of the human pelvic bone so as to span from a right iliac of the human pelvic bone to a pubic symphysis of the human pelvic bone, a second implant member being positioned adjacent to a left hemipelvis of the human pelvic bone independent of and while remaining separate and detached from the first implant so as to span from a left iliac of the human pelvic bone to the pubic symphysis of the human pelvic bone;

rigidly attaching the first proximal end of the first implant member to a bone at the iliac crest of a right hemipelvis by inserting one or more screws through one or more holes penetrating through a first proximal end of the first implant member and into underlying bone;

rigidly attaching the second proximal end of the second implant member to a bone at the iliac crest of a left hemipelvis by inserting one or more screws through one or more holes penetrating through a second proximal end of the second implant member and into underlying bone; and after independently positioning the first and second implant members while remaining separate and detached from each other, rigidly connecting a first medial end of the first implant member with a second medial end of the second implant member at a pubic symphysis with a clamp so that the first and second implant members maintain a curvature and relative structural positioning and stabilize the human pelvic bone so that a first end of the clamp is secured to the first medial end of the first implant member and a second end of the clamp is secured to the second medial end of the second implant member in order that the first and second medial ends are spaced apart, substantially parallel, and extend in opposing directions.

\* \* \* \* \*

UNITED STATES PATENT AND TRADEMARK OFFICE
CERTIFICATE OF CORRECTION

Page 1 of 2

PATENT NO. : 8,398,637 B2
APPLICATION NO. : 11/906849
DATED : March 19, 2013
INVENTOR(S) : Parsell et al.

It is certified that error appears in the above-identified patent and that said Letters Patent is hereby corrected as shown below:

In the Drawings

Drawing sheet 4 of 11, Fig. 9A should be replaced with the corrected Fig. 9A as shown here.

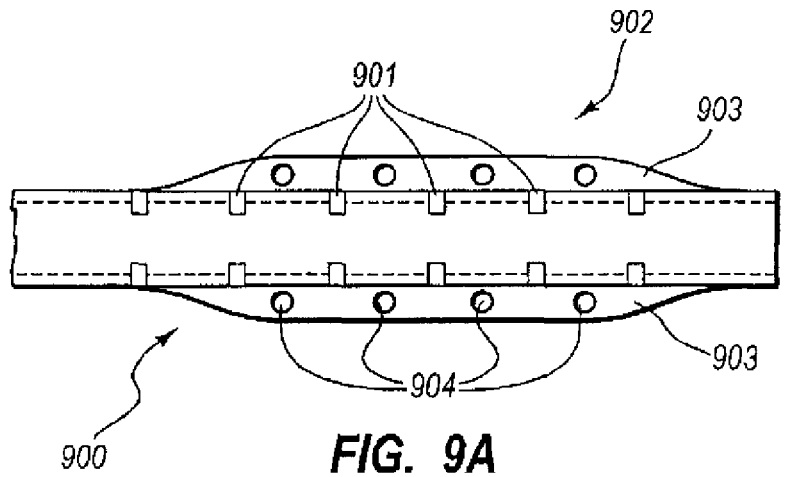

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,398,637 B2

Drawing sheet 10 of 11, Fig. 15 should be replaced with the corrected Fig. 15 as shown here.

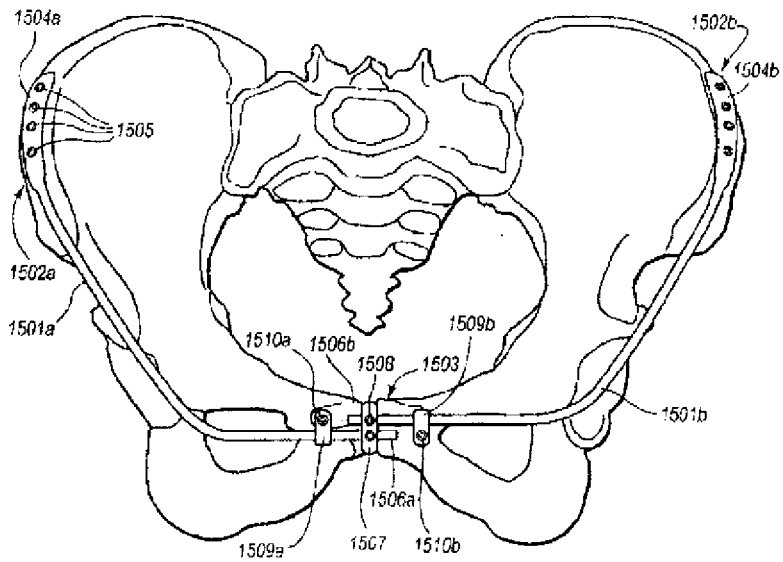

FIG. 15

In the Specification

Column 2
Lines 19-20, change "placement." to --placements.--
Line 67, change "vic." to --vic--

Column 3
Line 59, change "109 may" to --109 that may--

Column 4
Line 19, change "105, 203" to --102, 201--

Column 5
Line 18, change "device 1001" to --device 1101--
Line 26, change "illustrates" to --illustrate--
Line 46, change "tension" to --tension 1206--

UNITED STATES PATENT AND TRADEMARK OFFICE
CERTIFICATE OF CORRECTION

Page 1 of 3

PATENT NO. : 8,398,637 B2
APPLICATION NO. : 11/906849
DATED : March 19, 2013
INVENTOR(S) : Parsell et al.

It is certified that error appears in the above-identified patent and that said Letters Patent is hereby corrected as shown below:

Delete the title page and substitute therefore with the attached title page consisting of the corrected illustrative figure.

In the Drawings

Drawing sheet 4 of 11, Fig. 9A should be replaced with the corrected Fig. 9A as shown here.

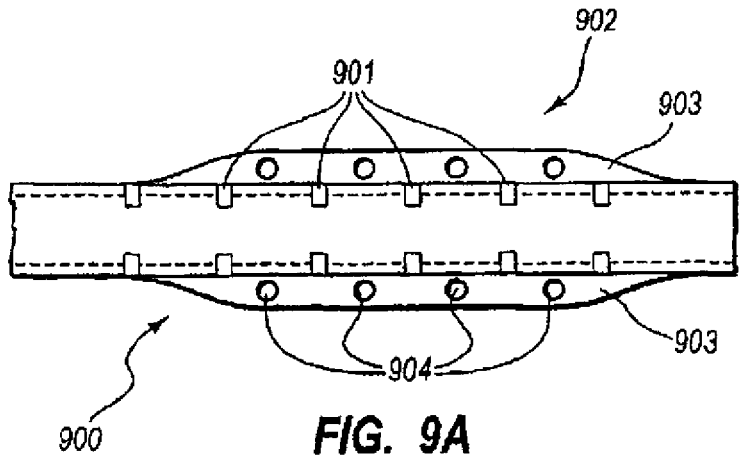

This certificate supersedes the Certificate of Correction issued March 11, 2014.

Signed and Sealed this
First Day of April, 2014

Michelle K. Lee
*Deputy Director of the United States Patent and Trademark Office*

Drawing sheet 10 of 11, Fig. 15 should be replaced with the corrected Fig. 15 as shown here.

In the Specification

Column 2
Lines 19-20, change "placement." to --placements.--.
Line 67, change "vic." to --vic--.

Column 3
Line 59, change "109 may" to --109 that may--.

Column 4
Line 19, change "105, 203" to --102, 201--.

Column 5
Line 18, change "device 1001" to --device 1101--.
Line 26, change "illustrates" to --illustrate--.
Line 46, change "tension" to --tension 1206--.

(12) United States Patent
Parsell et al.

(10) Patent No.: US 8,398,637 B2
(45) Date of Patent: Mar. 19, 2013

(54) DEVICE AND METHOD FOR LESS INVASIVE SURGICAL STABILIZATION OF PELVIC FRACTURES

(76) Inventors: Douglas Eric Parsell, Ridgeland, MS (US); Peter Alexander Cole, North Oaks, MN (US)

( * ) Notice: Subject to any disclaimer, the term of this patent is extended or adjusted under 35 U.S.C. 154(b) by 775 days.

(21) Appl. No.: 11/906,849

(22) Filed: Oct. 5, 2007

(65) Prior Publication Data

US 2008/0108989 A1 May 8, 2008

Related U.S. Application Data

(60) Provisional application No. 60/856,610, filed on Nov. 6, 2006.

(51) Int. Cl.
*A61B 17/58* (2006.01)

(52) U.S. Cl. ........................ 606/71; 606/281

(58) Field of Classification Search .......... 606/103, 606/254–278, 280, 282, 53, 60, 70, 71
See application file for complete search history.

(56) References Cited

U.S. PATENT DOCUMENTS

| | | | | |
|---|---|---|---|---|
| 2,406,832 A * | 9/1946 | Hardinge | ........ | 606/71 |
| 2,443,363 A * | 6/1948 | Townsend et al. | ........ | 606/71 |
| 2,486,303 A * | 10/1949 | Longfellow | ........ | 606/71 |
| 3,242,922 A * | 3/1966 | Thomas | ........ | 606/250 |
| 3,488,779 A * | 1/1970 | Christensen | ........ | 623/16.11 |
| 3,547,114 A * | 12/1970 | Haboush | ........ | 606/71 |
| 3,900,025 A * | 8/1975 | Barnes, Jr. | ........ | 606/71 |
| 4,292,964 A | 10/1981 | Ulrich | | |
| 4,327,715 A * | 5/1982 | Corvisier | ........ | 606/71 |
| 4,361,144 A | 11/1982 | Slatis | | |
| 4,454,876 A * | 6/1984 | Mears | ........ | 606/281 |
| 4,573,454 A * | 3/1986 | Hoffman | ........ | 606/250 |
| 4,573,458 A * | 3/1986 | Lower | ........ | 606/280 |
| 4,719,905 A * | 1/1988 | Steffee | ........ | 606/262 |
| 5,108,397 A * | 4/1992 | White | ........ | 606/60 |
| 5,336,224 A * | 8/1994 | Selman | ........ | 606/280 |
| 5,350,378 A | 9/1994 | Cole | | |
| 5,443,465 A * | 8/1995 | Pennig | ........ | 606/59 |
| 5,490,851 A * | 2/1996 | Nenov et al. | ........ | 606/252 |
| 5,507,745 A * | 4/1996 | Logroscino et al. | ........ | 606/261 |
| 5,527,310 A * | 6/1996 | Cole et al. | ........ | 606/60 |
| 5,582,612 A * | 12/1996 | Lin | ........ | 606/250 |
| 5,800,434 A * | 9/1998 | Campbell, Jr. | ........ | 606/279 |
| 5,810,815 A * | 9/1998 | Morales | ........ | 606/250 |
| 5,993,449 A * | 11/1999 | Schlapfer et al. | ........ | 606/60 |
| 6,129,728 A * | 10/2000 | Schumacher et al. | ........ | 606/71 |
| 6,162,222 A | 12/2000 | Poka | | |
| 6,183,476 B1 * | 2/2001 | Gerhardt et al. | ........ | 606/71 |
| 6,336,927 B2 * | 1/2002 | Rogozinski | ........ | 606/286 |
| 6,340,362 B1 | 1/2002 | Pierer | | |
| 6,440,131 B1 | 8/2002 | Haidukewych | | |
| 6,547,790 B2 * | 4/2003 | Harkey et al. | ........ | 606/250 |
| 6,589,250 B2 * | 7/2003 | Schendel | ........ | 606/105 |
| 6,832,999 B2 * | 12/2004 | Ueyama et al. | ........ | 606/264 |

(Continued)

OTHER PUBLICATIONS

Timothy G. Hiesterman, DO, Brian W. Hill MD, Peter A Cole MD, Surgical Technique: A percutaneous Method of Subcutaneous Fixation for the Anterior Pelvic Ring, Clinical Orthopaedics and Related Research (2012) 470:2116-2123.*

*Primary Examiner* — Eduardo C Robert
*Assistant Examiner* — Lynnsy Schneider
(74) *Attorney, Agent, or Firm* — Workman Nydegger

(57) ABSTRACT

An apparatus and method for minimally invasive stabilization of anterior pelvic fractures consisting of two rod shaped implants that may be surgically inserted subcutaneously or along the bone surface of each hemipelvis and a means of both linking the individual rods as well as rigidly securing the construct to the pelvis.

17 Claims, 11 Drawing Sheets